United States Patent
Katayama et al.

(10) Patent No.: US 6,335,026 B1
(45) Date of Patent: Jan. 1, 2002

(54) PESTICIDAL COMPOSITIONS

(75) Inventors: Yasuyuki Katayama, Toyonaka; Toshiro Ohtsubo, Sanda, both of (JP); Daniel C. Heffernan, North East, MD (US)

(73) Assignee: Sumitomo Chemical Co., Ltd., Osaka (JP)

( * ) Notice: Subject to any disclaimer, the term of this patent is extended or adjusted under 35 U.S.C. 154(b) by 0 days.

(21) Appl. No.: 08/220,882

(22) Filed: Mar. 31, 1994

(30) Foreign Application Priority Data

| Jun. 16, 1993 | (JP) | 5-144954 |
| Jun. 16, 1993 | (JP) | 5-144955 |
| Jun. 16, 1993 | (JP) | 5-144958 |

(51) Int. Cl.⁷ .................................................. A01N 25/03
(52) U.S. Cl. .................... 424/409; 424/405; 424/408; 424/421; 424/724; 514/120
(58) Field of Search ..................... 424/405, 408, 424/409, 421, 724; 514/120; 558/71, 72, 178

(56) References Cited

U.S. PATENT DOCUMENTS

| 2,962,418 A | * | 11/1960 | Sawyer | 424/421 |
| RE33,670 E | * | 8/1991 | Maglio | 424/408 |
| 5,100,667 A | | 3/1992 | Chan et al. | |
| 5,230,893 A | * | 7/1993 | Gotou et al. | 424/409 |
| 5,232,701 A | * | 8/1993 | Ogawa et al. | 424/408 |
| 5,369,100 A | | 11/1994 | Cummings | |

FOREIGN PATENT DOCUMENTS

| EP | 0415609 | | 3/1991 |
| EP | 0480679 | | 4/1992 |
| JP | 59078110 | | 5/1984 |
| JP | 63-45203 | * | 2/1988 |
| JP | 64-9 | | 1/1989 |

OTHER PUBLICATIONS

Merck: Boric Acid p. 160, 1962.*

* cited by examiner

*Primary Examiner*—Neil S. Levy
(74) *Attorney, Agent, or Firm*—Sughrue, Mion, Zinn, Macpeak & Seas, PLLC

(57) ABSTRACT

A solid pesticidal composition containing acephate is stabilized by adding thereto at least one stabilizer selected from the group consisting of boron oxide, metaboric acid, aluminum oxide and the calcined product of synthetic silicon dioxide.

25 Claims, No Drawings

PESTICIDAL COMPOSITIONS

The present invention relates to a stabilized solid pesticidal composition containing acephate.

Acephate (O,S-dimethyl acetylphosphoramidothioate) is an insecticidally active compound as described in the page 1 of The Pesticide Manual 8th edition (published from the British Crop Protection Council in 1987). Since this compound is effective to control various pests, it is now used as an active ingredient for agricultural pesticides.

However, acephate in pesticidal compositions is not so high in its stability, so that acephate in the compositions decomposes violently depending upon storage conditions. As a result, there is a case where the pesticidal activity of acephate cannot be used effectively.

Therefore, there has been a demand for the development of stabilized pesticidal compositions containing acephate.

The present invention is based on the discovery that solid pesticidal compositions containing acephate may be stabilized by adding thereto at least one of boron oxide, metaboric acid, aluminum oxide and the calcined product of synthetic silicon dioxide. The present invention provides a stabilized solid pesticidal composition containing acephate and a method for stabilizing the composition.

The amount of at least one boron oxide, metaboric acid and aluminum oxide effective to stabilize acephate is generally 0.01 to 0.5 part by weight to 1 part by weight of acephate. Of course, a higher amount thereof may be used.

When the calcined product of synthetic silicon dioxide is used as the stabilizer, the amount of the stabilizer added is generally 0.05 part by weight or more to 1 part by weight of acephate.

The calcined product of synthetic silicon dioxide used in the present invention is usually produced by adding a mineral acid such as hydrochloric acid and sulfuric acid to an aqueous sodium silicate solution to sodium silicate solution to precipitate synthetic silicon dioxide and then calcining this precipitate at 600° C. to 900° C., preferably 700° C. to 800° C. Commercially available products such as Carplex CS-7 (produced by Shionogi & Co., Ltd.), Carplex CS-5 (produced by Shionogi & Co., Ltd.) and Finesil P-8 (produced by Tokuyama Soda Co., Ltd.) may be used as they are.

The solid pesticidal composition stabilized by the present invention usually contains (a) acephate, (b) at least one boron oxide, metaboric acid, aluminum oxide and the calcined product of synthetic silicon dioxide and (c) a solid carrier for formulation. When the calcined product of synthetic silicon dioxide is used as the stabilizer, these stabilizers may be used as a solid carrier for formulation.

The content of acephate in the above solid pesticidal composition is generally 0.5 to 99 wt. %, preferably 5 to 95 wt. %, and the content of boron oxide, metaboric acid and/or aluminum oxide used as the stablizer, is an amount sufficient to stabilize acephate, i.e. usually 0.01 to 50 wt. %, preferably 0.1 to 20 wt. %, more preferably 1 to 10 wt. %.

When the calcined product of synthetic silicon dioxide is used as the stabilizer, the content of acephate in the solid pesticidal composition stabilized by the present invention is generally 0.5 to 99 wt. %, preferably 5 to 95 wt. %, and the content of the calcined product of synthetic silicon dioxide used is an amount which can stabilize acephate, usually 1 to 99 wt. %.

The solid carrier for formulation used in the present invention includes inorganic carriers such as kaolin clay, attapulgite clay, sericite clay, pyrophyllite clay, montmorillonite clay, zeolite, bentonite, acid clay, activated clay, serpentine, talc and diatomaceous earth, inorganic salts such as sulfates, nitrates and chlorides and synthetic carriers such as silica; and organic carriers such as sugars, starch, dextrin, flour, soybean powder, corn powder, and wood powder. These solid carriers for formulation are contained in the solid pesticidal composition of the present invention in an amount of usually 1 to 90 wt. %, preferably 20 to 70 wt. %.

If necessary, the above solid pesticidal composition may further contain various kinds of auxiliary for pesticidal composition. The auxiliary for pesticidal composition includes surface active agents, coloring agents, perfumes, known stabilizers and the like. These auxiliaries may be contained in the solid pesticidal composition of the present invention in an amount of usually 0.1 to 35 wt. %, preferably 2 to 10 wt. %.

The surface active agents include for example anionic surface active agents such as the salt of alkyl sulfate (e.g. sodium lauryl sulfate), alkylarylsulfonates (e.g. sodium alkylnaphthalenesulfonate), lignosulfonates (e.g. sodium lignosulfonate), succinic acid ester derivatives, the salt of the ester of polyethylene glycol alkylaryl ether with sulfuric acid and aromatic sulfonate/formaldehyde condensates, and nonionic surface active agents such as polyoxyethylene alkyl ether, polyoxyethylene alkylaryl ether, and polyoxyethylene arylaryl ether.

The above solid pesticidal composition may further contain other active ingredients, for example, pyrethroid compounds such as fenpropathrin and fenvalerate.

The above solid pesticidal composition may be produced according to the conventional methods, for example, by admixing acephate, stabilizer, solid carrier for formulation and if necessary auxiliaries for formulation such as surface active agents in a mixer, and pulverizing the mixture with a pulverizer, for example, air mills, hammer mills or centrifugal pulverizers or by molding the resulting pulverized product into granules with compression molding presses, e.g., roller compacters, extrusion granulators and pan granulators.

The present invention will be illustrated in more detail with reference to the following formulation examples and test examples, but it is not to be interpreted as being limited to the following examples alone.

FORMULATION EXAMPLE 1

Fifty parts by weight of acephate, 5 parts by weight of boron oxide and 45 parts by weight of Wessalon S (synthetic silicon dioxide produced by Degussa Co.) are mixed in a mixer, and the resulting mixture is finely pulverized with a centrifugal pulverizer to obtain a wettable powder which is a solid pesticidal composition of the present invention.

FORMULATION EXAMPLE 2

Fifty parts by weight of acephate, 5 parts by weight of boron oxide and 45 parts by weight of Tokusil GU-N (synthetic silicon dioxide produced by Tokuyama Soda Co., Ltd.) are mixed in a mixer, and the resulting mixture is finely pulverized with a centrifugal pulverizer to obtain a wettable powder which is a solid pesticidal composition of the present invention.

FORMULATION EXAMPLE 3

Fifty parts by weight of acephate, 5 parts by weight of boron oxide and 45 parts by weight of Hi-Sil 233 (synthetic silicon dioxide produced by PPG) are mixed in a mixer, and the resulting mixture is finely pulverized with a centrifugal pulverizer to obtain a wettable powder which is a solid pesticidal composition of the present invention.

FORMULATION EXAMPLE 4

Twenty-five parts by weight of acephate, 10 parts by weight of boron oxide and 65 parts by weight of ammonium sulfate are mixed in a mixer, and the resulting mixture is finely pulverized with a centrifugal pulverizer to obtain a wettable powder which is a solid pesticidal composition of the present invention.

FORMULATION EXAMPLE 5

Seventy-five parts by weight of acephate, 10 parts by weight of boron oxide and 15 parts by weight of ammonium sulfate are mixed in a mixer, and the resulting mixture is finely pulverized with a centrifugal pulverizer to obtain a wettable powder which is a solid pesticidal composition of the present invention.

FORMULATION EXAMPLE 6

Twenty-five parts by weight of acephate, 5 parts by weight of boron oxide, 5 parts by weight of sodium dodecylbenzenesulfonate and 65 parts by weight of diatomaceous earth are mixed in a mixer, and the resulting mixture is finely pulverized with a centrifugal pulverizer to obtain a wettable powder which is a solid pesticidal composition of the present invention.

FORMULATION EXAMPLE 7

Forty parts by weight of acephate, 10 parts by weight of metaboric acid, 10 parts by weight of ammonium sulfate and 40 parts by weight of Hi-Sil 233 (described above) are mixed in a mixer, and the resulting mixture is finely pulverized with a centrifugal pulverizer to obtain a wettable powder which is a solid pesticidal composition of the present invention.

FORMULATION EXAMPLE 8

Forty parts by weight of acephate, 10 parts by weight of aluminum oxide, 10 parts by weight of ammonium sulfate and 40 parts by weight of Hi-Sil 233 are mixed in a mixer, and the resulting mixture is finely pulverized with a centrifugal pulverizer to obtain a wettable powder which is a solid pesticidal composition of the present invention.

FORMULATION EXAMPLE 9

Twenty-five parts by weight of acephate, 5 parts by weight of aluminum oxide, 5 parts by weight of sodium dodecylbenzenesulfonate and 65 parts by weight of diatomaceous earth are mixed in a mixer, and the resulting mixture is finely pulverized with a centrifugal pulverizer to obtain a wettable powder which is a solid pesticidal composition of the present invention.

FORMULATION EXAMPLE 10

Fifty parts by weight of acephate and 50 parts by weight of Carplex CS-7 are mixed in a mixer, and the resulting mixture is finely pulverized with a centrifugal pulverizer to obtain a wettable powder which is a solid pesticidal composition of the present invention.

FORMULATION EXAMPLE 11

Fifty parts by weight of acephate and 50 parts by weight of Carplex CS-5 are mixed in a mixer, and the resulting mixture is finely pulverized with a centrifugal pulverizer to obtain a wettable powder which is a solid pesticidal composition of the present invention.

FORMULATION EXAMPLE 12

Fifty parts by weight of acephate and 50 parts by weight of Finesil P-8 are mixed in a mixer, and the resulting mixture is finely pulverized with a centrifugal pulverizer to obtain a wettable powder which is a solid pesticidal composition of the present invention.

FORMULATION EXAMPLE 13

Ten parts by weight of acephate and 90 parts by weight of Finesil P-8 are mixed in a mixer, and the resulting mixture is finely pulverized with a centrifugal pulverizer to obtain a wettable powder which is a solid pesticidal composition of the present invention.

FORMULATION EXAMPLE 14

Twenty parts by weight of acephate and 80 parts by weight of Finesil P-8 are mixed in a mixer, and the resulting mixture is finely pulverized with a centrifugal pulverizer to obtain a wettable powder which is a solid pesticidal composition of the present invention.

FORMULATION EXAMPLE 15

Seventy-five parts by weight of acephate and 25 parts by weight of Finesil P-8 are mixed in a mixer, and the resulting mixture is finely pulverized with a centrifugal pulverizer to obtain a wettable powder which is a solid pesticidal composition of the present invention.

FORMULATION EXAMPLE 16

Ninety parts by weight of acephate and 10 parts by weight of Finesil P-8 are mixed in a mixer, and the resulting mixture is finely pulverized with a centrifugal pulverizer to obtain a wettable powder which is a solid pesticidal composition of the present invention.

FORMULATION EXAMPLE 17

Twenty-five parts by weight of acephate, 5 parts by weight of sodium dodecylbenzenesulfonate and 70 parts by weight of Carplex CS-7 are mixed in a mixer, and the resulting mixture is finely pulverized with a centrifugal pulverizer to obtain a wettable powder which is a solid pesticidal composition of the present invention.

FORMULATION EXAMPLE 18

Twenty-five parts by weight of acephate, 5 parts by weight of polyoxyethylene nonylphenyl ether and 70 parts by weight of Carplex CS-7 are mixed in a mixer, and the resulting mixture is finely pulverized with a centrifugal pulverizer to obtain a wettable powder which is a solid pesticidal composition of the present invention.

FORMULATION EXAMPLE 19

Fifty parts by weight of acephate and 50 parts by weight of Finesil P-8 are mixed in a mixer, and finely pulverized product is compression-granulated with a roller compacter and disintegrated into a particle size of 0.3 to 1.2 mm to obtain a granular wettable powder which is a solid pesticidal composition of the present invention.

TEST EXAMPLE 1

Each of the wettable powders obtained in Formulation Examples 1, 2 and 3 was put air-tightly in a 50-ml glass ampoule and stored for 2 weeks in a 60° C. incubator. The content of acephate in the composition before and after storage was measured using a gas chromatography, and the decomposition rate was obtained from the following equation:

$$\text{Decomposition rate (\%)} = 100 - 100 \times \frac{\text{acephate content after storage}}{\text{acephate content before storage}}.$$

Comparative compositions 1, 2 and 3 were prepared in the same manner as in Formulation Examples 1, 2 and 3, respectively, except that 5 parts by weight of boron oxide was replaced by 5 parts by weight of Wessalon S, Tokusil GU-N and Hi-Sil 233, respectively. Thereafter, the decomposition rate of these comparative compositions was obtained in the same manner as above. The results are shown in Table 1.

TABLE 1

| Test composition | Decomposition rate (%) |
| --- | --- |
| Composition of Formulation Example 1 | 3 |
| Composition of Formulation Example 2 | 10 |
| Composition of Formulation Example 3 | 9 |
| Comparative composition 1 | 30 |
| Comparative composition 2 | 42 |
| Comparative composition 3 | 36 |

TEST EXAMPLE 2

The decomposition rate of the wettable powders obtained in Formulation Examples 4 and 5 was obtained by the same procedure as in Test Example 1.

Also, comparative compositions 4 and 5 were prepared in the same manner as in Formulation Examples 4 and 5, respectively, except that 10 parts by weight of boron oxide was replaced by 10 parts by weight of ammonium sulfate, and their decomposition rate was obtained in the same manner as above. The results are shown in Table 2.

TABLE 2

| Test composition | Decomposition rate (%) |
| --- | --- |
| Composition of Formulation Example 4 | 8 |
| Composition of Formulation Example 5 | 2 |
| Comparative composition 4 | 45 |
| Comparative composition 5 | 31 |

TEST EXAMPLE 3

The decomposition rate of the wettable powder obtained in FORMULATION EXAMPLE 6 was obtained by the same procedure as in Test Example 1.

Also, a comparative composition 6 was prepared in the same manner as in Formulation Example 6 except that 5 parts by weight of boron oxide was replaced by 5 parts by weight of diatomaceous earth, and its decomposition rate was obtained in the same manner as above. The results are shown in Table 3.

TABLE 3

| Test composition | Decomposition rate (%) |
| --- | --- |
| Composition of Formulation Example 6 | 7 |
| Comparative composition 6 | 33 |

TEST EXAMPLE 4

The decomposition rate of the wettable powder obtained in Formulation Example 7 was obtained by the same procedure as in Test Example 1.

Also, a comparative composition 7 was prepared in the same manner as in Formulation Example 7 except that 10 parts by weight of metaboric acid was replaced by 10 parts by weight of Hi-Sil 233, and its decomposition rate was obtained in the same manner as above. The results are shown in Table 4.

TABLE 4

| Test composition | Decomposition rate (%) |
| --- | --- |
| Composition of Formulation Example 7 | 3 |
| Comparative composition 7 | 43 |

TEST EXAMPLE 5

The decomposition rate of the wettable powder obtained in Formulation Example 8 was obtained by the same procedure as in Test Example 1.

Also, a comparative composition 8 was prepared in the same manner as in Formulation Example 8 except that 10 parts by weight of aluminum oxide was replaced by 10 parts by weight of Hi-Sil 233, and its decomposition rate was obtained in the same manner as above. The results are shown in Table 5.

TABLE 5

| Test composition | Decomposition rate (%) |
| --- | --- |
| Composition of Formulation Example 8 | 4 |
| Comparative composition 8 | 43 |

TEST EXAMPLE 6

The decomposition rate of the wettable powders obtained in Formulation Examples 10, 11 and 12 was obtained by the same procedure as in Test Example 1.

Also, a comparative compositions 9, 10, 11 and 12 were prepared in the same manner as in Formulation Example 10 except that 50 parts by weight of Carplex CS-7 was replaced by 50 parts by weight of Tokusil GU-N, Carplex 80, Hi-Sil 233 and Wessalon S, respectively. And, the decomposition rate of these comparative compositions was obtained in the same manner as above. The results are shown in Table 6.

TABLE 6

| Test composition | Decomposition rate (%) |
| --- | --- |
| Composition of Formulation Example 10 | 7 |
| Composition of Formulation Example 11 | 9 |
| Composition of Formulation Example 12 | 10 |
| Comparative composition 9 | 42 |
| Comparative composition 10 | 39 |
| Comparative composition 11 | 36 |
| Comparative composition 12 | 35 |

TEST EXAMPLE 7

The decomposition rate of the wettable powders obtained in Formulation Examples 13, 14, 15 and 16 was obtained by the same procedure as in Test Example 1.

Also, a comparative compositions 13, 14, 15 and 16 were prepared in the same manner as in Formulation Examples 13, 14, 15 and 16, respectively, except that Finesil P-8 was replaced by Tokusil GU-N, and the decomposition rate of these comparative compositions was obtained in the same manner as above. The results are shown in Table 7.

TABLE 7

| Test composition | Decomposition rate (%) |
| --- | --- |
| Composition of Formulation Example 13 | 12 |
| Composition of Formulation Example 14 | 9 |
| Composition of Formulation Example 15 | 6 |
| Composition of Formulation Example 16 | 3 |
| Comparative composition 13 | 65 |
| Comparative composition 14 | 48 |
| Comparative composition 15 | 35 |
| Comparative composition 16 | 31 |

TEST EXAMPLE 8

The decomposition rate of the wettable powders obtained in Formulation Examples 17 and 18 was obtained by the same procedure as in Test Example 1.

Also, a comparative compositions 17 and 18 were prepared in the same manner as in Formulation Examples 17 and 18, respectively, except that Carplex CS-7 was replaced by Carplex 80, and the decomposition rate of these comparative compositions was obtained in the same manner as above. The results are shown in Table 8.

TABLE 8

| Test composition | Decomposition rate (%) |
| --- | --- |
| Composition of Formulation Example 17 | 11 |
| Composition of Formulation Example 18 | 9 |
| Comparative composition 17 | 38 |
| Comparative composition 18 | 40 |

TEST EXAMPLE 9

The decomposition rate of the wettable powder obtained in Formulation Example 19 was obtained by the same procedure as in Test Example 1.

Also, a comparative composition 19 was prepared in the same manner as in Formulation Example 19 except that Finesil P-8 was replaced by Hi-Sil 233, and its decomposition rate was obtained in the same manner as above. The results are shown in Table 9.

TABLE 9

| Test composition | Decomposition rate (%) |
| --- | --- |
| Composition of Formulation Example 19 | 7 |
| Comparative composition 19 | 37 |

What is claimed is:

1. A method for ameliorating decomposition of acephate in a solid, pesticidal composition which comprises adding an effective amount of at least one stabilizer selected from the group consisting of boron oxide, metaboric acid, aluminum oxide and the calcined product of synthetic silicone dioxide to said acephate.

2. A method according to claim 1, wherein the stabilizer is boron oxide.

3. A method according to claim 1, wherein the stabilizer is metaboric acid.

4. A method according to claim 1, wherein the stabilizer is aluminum oxide.

5. A method according to claim 1, wherein the stabilizer is the calcined product of synthetic silicon dioxide.

6. A solid pesticidal composition which comprises:
   (a) acephate as an active ingredient,
   (b) an effective amount of at least one stabilizer selected from the group consisting of boron oxide, metaboric acid, aluminum oxide, and the calcined product of synthetic silicon dioxide for stabilizing said acephate, and
   (c) a solid carrier for formation.

7. A solid pesticidal composition according to claim 6, wherein the stabilizer is boron oxide.

8. A solid pesticidal composition according to claim 7, wherein the amount of acephate in the composition is 5 to 95 wt. % and the amount of boron oxide is 0.1 to 20 wt. %.

9. A solid pesticidal composition according to claim 6, wherein the stabilizer is metaboric acid.

10. A solid pesticidal composition according to claim 9, wherein the amount of acephate in the composition is 5 to 95 wt. % and the amount of metaboric acid is 0.1 to 20 wt. %.

11. A solid pesticidal composition according to claim 6, wherein the stabilizer is aluminum oxide.

12. A solid pesticidal composition according to claim 11, wherein the amount of acephate in the composition is 5 to 95 wt. % and the amount of aluminum oxide is 0.1 to 20 wt. %.

13. A solid pesticidal composition according to claim 6, wherein the stabilizer is the calcined product of synthetic silicon dioxide.

14. A solid pesticidal composition according to claim 13, wherein the amount of acephate in the composition is 5 to 95 wt. % and the amount of the calcined product of synthetic silicon dioxide is 1 to 99 wt. %.

15. A solid pesticidal composition consisting essentially of
   (a) acephate as an active ingredient,
   (b) an effective amount of at least one stabilizer selected from the group consisting of boron oxide, metaboric acid, aluminum oxide, and the calcined product of synthetic silicon dioxide for stabilizing said acephate, and
   (c) a solid carrier for formulation.

16. A solid pesticidal composition comprising
(a) acephate as an active ingredient, and
(b) an effective amount of at least one stabilizer selected from the group consistinq of boron oxide, metaboric acid, and aluminum oxide, and the calcined product of synthetic silicone dioxide for stabilizing said acephate.

17. A solid pesticidal composition consisting essentially essentially of
(a) acephate as an active ingredient,
(b) an effective amount of at least one stabilizer selected form the group consisting of boron oxide, metaboric acid, aluminum oxide, and the calcined product of synthetic silicon dioxide for stabilizing said acephate.

18. A solid pesticidal composition according to claim 17, wherein the amount of component (a) is 0.5 to 99 wt. %, the amount of component (b) is 0.01 to 50 wt. %, and the weight ratio of component (a) and component (b) is 1:0.01 or more when component (b) is boron oxide, metaboric acid, or aluminum oxide; and
wherein the amount of component (a) is 0.5 to 99 wt. %, the amount of component (b) is 1 to 99 wt. %, the weight ratio of component (a) and component (b) is 1:0.05 or more when component (b) is the calcined product of synthetic silicone dioxide in the solid pesticidal composition.

19. The solid pesticidal composition according to claim 15, wherein the amount of component (a) is 0.5 to 99 wt. %, the amount of component (b) is 0.01 to 50 wt. %, and the weight ratio of component (a) and component (b) is 1:0.01 or more when component (b) is selected from the group consisting of boron oxide, metaboric acid and aluminum oxide;
and wherein component (a) is 0.5 to 99 wt. %, the amount of component (b) is 1 to 99 wt. %, and the weight ratio of component (a) and component (b) is 1 : 0.05 or more when component (b) is the calcined product of synthetic silicon dioxide in the solid pesticidal composition.

20. A solid pesticidal composition consisting essentially of
(a) acephate as an active ingredient,
(b) an effective amount of at least one stabilizer selected from the group consisting of boron oxide, metaboric acid, aluminum oxide, and the calcined product of synthetic silicon dioxide for stabilizing said acephate, and
(c) a surface active agent.

21. A solid pesticidal composition according to claim 20 wherein the amount of component (a) is 0.5 to 99 wt. %, the amount of component (b) is 0.01 to 50 wt. %, and the weight ratio of component (a) and component (b) is 1:0.01 or more when (b) is selected from the group consisting of boron oxide, metaboric acid, or aluminum oxide; and
wherein the amount of component (a) is 0.5 to 99 wt. %, the amount of component (b) is 1 to 99 wt. %, the weight ratio of component (a) and component (b) is 1 : 0.05 or more when component (b) is the calcined product of synthetic silicon dioxide, and
said composition further contains, as component (d), at least one member selected from the group consisting of a coloring agent and perfume in an amount of 0.1 to 35 wt. % in the solid pesticidal composition.

22. A solid pesticidal composition consisting essentially of
(a) acephate as an active ingredient,
(b) an effective amount of at least one stabilizer selected from the group consisting of boron oxide, metaboric acid, aluminum oxide, and the calcined product of synthetic silicon dioxide for stabilizing acephate,
(c) a solid carrier except a carbonate and solid acid, and
(d) a surface active agent.

23. A solid pesticidal composition according to claim 22, wherein the amount of component (a) is 0.5 to 99 wt. %, the amount of component (b) is 0.01 to 50 wt. %, and the weight ratio of component (a) and component (b) is 1:0.01 or more when component (b) is selected from the group consisting of boron oxide, metaboric acid and aluminum oxide; and
wherein the amount of component (a) is 0.5 to 99 wt. %, the amount of component (b) is 1 to 99 wt. %, the weight of the ratio of component (a) and component (b) is 1:0.05 or more when the component (b) is the calcined product of synthetic silicon dioxide, and
wherein the amount of component (c) is 1 to 90 wt. %, and the amount of component (d) is 0.1 to 35 wt. % in the pesticidal composition.

24. A solid pesticidal composition consisting essentially of
(a) an effective amount of an acephate and a pyrethroid compound as active ingredients,
(b) an effective amount of at least one stabilizer selected from the group consisting of boron oxide, metaboric acid, aluminum oxide and the calcined product of synthetic silicon dioxide for stabilizing acephate,
(c) a solid carrier, and
(d) a surface active agent.

25. The method for preventing decomposition of acephate in a solid pesticdal composition according to claim 1 wherein said stabilizer is present in an amount of 0.05 parts by weight or more to 1 part by weight of said acephate when said stabilizer is the calcined product of synthetic silicon dioxide,
and wherein said stabilizer is present in an amount of 0.01 to 0.5 parts by weight to 1 part by weight of acephate when said stabilizer is selected from the group consisting of boron oxide, metaboric acid, and aluminum oxide.

* * * * *